United States Patent
Quallich

Patent Number: 5,552,548
Date of Patent: Sep. 3, 1996

[54] ENANTIOSELECTIVE OXAZABOROLIDINE CATALYSTS

[75] Inventor: George J. Quallich, North Stonington, Conn.

[73] Assignee: Pfizer Inc., New York, N.Y.

[21] Appl. No.: 318,828

[22] Filed: Oct. 13, 1994

Related U.S. Application Data

[63] Continuation of PCT/US93/00687, Feb. 1, 1993, which is a continuation of Ser. No. 883,317, May 14, 1992, abandoned.

[51] Int. Cl.⁶ .................... C07B 53/00; C07F 5/02
[52] U.S. Cl. .................... 546/13; 548/405; 548/950; 558/289; 568/881
[58] Field of Search ............ 546/13, 344; 548/146, 548/215, 405, 950; 568/6, 715, 808, 822, 881; 558/289

[56] References Cited

U.S. PATENT DOCUMENTS 4,943,635   7/1990   Corey ........................ 546/13

FOREIGN PATENT DOCUMENTS

0453288A1   10/1991   European Pat. Off. .
0453298A2   10/1991   European Pat. Off. .

OTHER PUBLICATIONS

Itsuno et al., J. of the Chemical Society, Chemical Communications, 1983, 469–70.
Saigo et al., Bull. Chem. Soc., Japan, 1982, 55, 1568–73.
Youn et al., Tetrahedron Letters, 1988, 29, 4453–6.
Rao et al., Tetrahedron Letters, 1990, 31, 2341–44.
Stingl et al., Tetrahedron: Asymmetry, 1992, 3, 223–6.
Martens et al., Tetrahedron: Asymmetry, 1992, 3, 347–50.
Wallbaum et al., Tetrahedron: Asymmetry, 1991, 2, 1093–96.
Wallbaum and Martens, Tetrahedron: Asymmetry, 1992, 3, 1475–1504.

*Primary Examiner*—Shean C. Wu
*Attorney, Agent, or Firm*—Peter C. Richarson; Gregg C. Benson; Robert T. Ronau

[57] ABSTRACT

The borane reduction of prochiral ketones to optically pure alcohols is effectively achieved by the utilization of catalytic amounts of the new and valuable oxazaborolidine catalysts of formula (I).

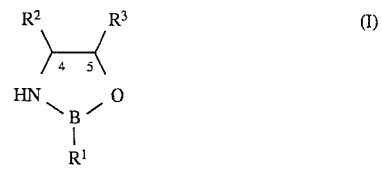

11 Claims, No Drawings

"5,552,548"

ENANTIOSELECTIVE OXAZABOROLIDINE CATALYSTS

This is a continuation of copending International Application Number PCT/US93/00687, filed 01 Feb. 1993, entitled "Enantioselective Oxazaborolidine Catalysts," which is a continuation of U.S. Ser. No. 07/883,317, filed 14 May 1992, entitled "Enantioselective Oxazaborolidine Catalysts" (now abandoned).

BACKGROUND OF THE INVENTION

This invention relates to the enantioselective reduction of prochiral ketones using a borane reducing agent in the presence of a novel and valuable chiral oxazaborolidine catalyst and to certain of said chiral oxazaborolidine catalysts useful in said reduction.

The enantioselective reduction of prochiral ketones to yield substantially enantiomerically pure alcohols has long been a goal of synthetic organic chemists. A number of reagents have been reported which effect such a transformation. (See, for example, Corey, U.S. Pat. No. 4,943,635, the subject matter of which is incorporated herein by reference). However, these methods suffer from one or more of the following drawbacks: (a) unacceptable amounts of the undesired enantiomer present as an impurity with the product; (b) low yields of alcohol; (c) difficulty of carrying out the reaction; (d) expense of preparing the catalyst; (e) difficulty in preparing the catalyst; or (f) inapplicability to a wide range of substituted prochiral ketones.

The previously disclosed (see, for example, Corey, supra, Merck, European Patent Application Nos. 0 453 288 A1 and 0 453 298 A2) enantioselectively effective oxazaborolidine catalysts are disubstituted at the carbon atom attached directly to the oxygen atom of the catalyst (e.g., the $C_5$ carbon atom of formula (I) below). When said carbon atom is not disubstituted, the product of the reduction reaction is much less optically pure (see Martens, et al., Tetrahedron:Asymmetry, 3, 347–50 (1992)).

It is therefore an object of this invention to provide chiral oxazaborolidine compounds which are capable of directing the enantioselective reduction of prochiral ketones to generate substantially enantiomerically pure alcohols.

It is a further object of this invention to provide said chiral oxazaborolidine compounds which are easily prepared from relatively inexpensive starting materials or readily available starting materials.

It is a still further object of this invention to provide a method of using said chiral oxazaborolidine compounds as catalysts for the enantioselective reduction of prochiral ketones to afford substantially enantiomerically pure alcohols.

SUMMARY OF THE INVENTION

This invention provides a chiral oxazaborolidine compound of the formula

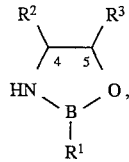

I wherein $R^1$ is hydrogen, $(C_1-C_8)$alkyl, benzyl, phenyl or phenyl variously substituted with up to three $(C_1-C_8)$alkyl, $(C_1-C_8)$alkoxy or halo groups such as chloro or fluoro; and $R^2$ and $R^3$ are syn and are each identically phenyl or phenyl variously substituted with up to three $(C_1-C_8)$alkyl, $(C_1-C_8)$alkoxy or halo groups such as chloro or fluoro.

A preferred group of compounds of this invention is the group of compounds of formula (I) wherein the $C_4$ carbon atom has the R configuration and the $C_5$ carbon atom has the S configuration.

Especially preferred within the preferred group is the compound wherein $R^2$ and $R^3$ are each phenyl and $R^1$ is methyl.

A second preferred group of compounds of this invention is the group of compounds of formula I wherein the $C_4$ carbon atom has the S configuration and the $C_5$ carbon atom has the R configuration.

Especially preferred within the second preferred group is the compound wherein $R^2$ and $R^3$ are each phenyl and $R^1$ is methyl.

This invention further provides for borane compounds of the formula

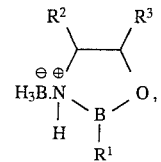

II wherein $R^1$ is hydrogen, $(C_1-C_8)$alkyl, benzyl, phenyl or phenyl or phenyl variously substituted with up to three $(C_1-C_8)$alkyl, $(C_1-C_8)$alkoxy or halo groups such as chloro or fluoro; and $R^2$ and $R^3$ are syn and are each identically phenyl or phenyl variously substituted with up to three $(C_1-C_8)$alkyl, $(C_1-C_8)$alkoxy or halo groups such as chloro or fluoro.

This invention still further provides a method for enantioselectively reducing a prochiral ketone comprising reacting said ketone with a borane reducing agent in the presence of a chiral oxazaborolidine compound of formula (I) in a reaction inert solvent at a temperature of from about 0° C. to about 50° C. for about 5 minutes to about 24 hours.

DETAILED DESCRIPTION OF THE INVENTION

The compounds of formula (I) of the present invention are readily prepared. Thus a single enantiomer of a 1,2-diaryl-2-aminoethanol derivative is suspended in a reaction inert solvent such as tetrahydrofuran, xylene, toluene, benzene, chlorobenzene or the like and is heated to a temperature of from about 60° C. to about boiling, preferably to about 60° C. The reaction mixture is stirred for from about 5 minutes to about 15 minutes at this temperature; preferred is the amount of time necessary to obtain complete dissolution of the diarylethanol derivative. The reaction mixture is then treated with borane, a trialkyl boroxine, a triarylboroxine, an alkyl boronic acid or an aryl boronic acid and is cooled to room temperature. Suitable boroxines for this reaction include boroxines of the formula

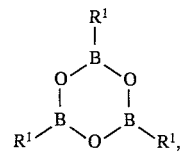

III wherein $R^1$ is $(C_1-C_8)$alkyl, benzyl, phenyl or phenyl variously substituted with up to three $(C_1-C_8)$alkyl, ($C_1$–$C_8$)alkoxy or halo groups such as chloro or fluoro. The reaction mixture is stirred for about one hour to about 24 hours, preferably for about 18 hours at room temperature. The oxazaborolidine compound of formula (I) is then isolated by the removal of water and excess boroxine where necessary and utilizing the standard techniques well known to one of ordinary skill in the art of synthetic organic chemistry.

The diarylaminoethanol derivative is prepared using well known chemistry. Thus, generally the appropriate benzaldehyde derivative is reacted under the conditions of a benzoin condensation, e.g., with catalytic potassium cyanide in a suitable reaction inert solvent to form the diaryl α-hydroxy ketone. Said α-hydroxy ketone is reacted with hydroxylamine to form the oxime, which is then reduced via catalytic hydrogenation to afford the racemic diarylaminoethanol derivative. Said racemic diarylaminoethanol derivative is resolved according to the usual resolution procedures of organic chemistry.

The boroxine derivatives used herein are also readily prepared when not readily available. Reaction of a trialkyl- or triarylborane with boron oxide under reflux for about 24 hours to about 48 hours in an inert atmosphere conveniently prepares the trialkyl or triarylboroxine derivatives. Alternatively, reaction of borane, a trialkyl borate or a triarylborate with a suitable Grignard reagent of the formula R-Mg-X wherein R is ($C_1$–$C_8$)alkyl, benzyl, phenyl or phenyl variously substituted with up to three ($C_1$–$C_8$)alkyl, ($C_1$–$C_5$)alkoxy or halo groups such as chloro or fluoro in a suitable reaction inert solvent such as tetrahydrofuran or diethyl ether at about –20° C. to about 50° C. affords the R-substituted boronic acid upon workup. Continued reflux utilizing a Dean-Stark trap to remove water generates the R-substituted boroxine derivative.

The boronic acids which are used herein are prepared as described in the foregoing paragraph or are prepared by the method recited by Corey, supra, or according to the references cited therein.

The process of the present invention is carried out by reacting a prochiral ketone of the formula $R^4R^5CO$, wherein $R^4$ and $R^5$ are defined hereinbelow with a borane reducing agent in the presence of a chiral oxazaborolidine catalyst according to formula (I). Said process results in the enantioselective reduction of said prochiral ketone, such that only one of two possible alcohol enantiomers is formed in preference to the corresponding enantiomer. The degree of enantio-selectivity which is obtained will vary depending upon the size of the $R^4$ and $R^5$ groups attached to the carbonyl group forming the prochiral ketone. When the $R^4$ and $R^5$ groups are similar in size, the degree of enantioselection will be lower. As the $R^4$ and $R^5$ groups become increasingly disparate in size, the degree of enantio-selection will be greater. However, it should be understood that the size of the $R^4$ and $R^5$ groups is not the sole determining factor affecting the degree of enantioselectivity achieved. Ordinarily, with prochiral ketones wherein $R^4$ and $R^5$ are at least moderately different in size, the desired enantiomer will be obtained in at least 80% enantiomeric excess (e.e.). Usually, however, far better enantiomeric excesses are obtained such as 90% e.e. or higher.

The prochiral ketone is dissolved in a suitable reaction inert solvent such as diethyl ether, dioxane, tetrahydrofuran or the like. Preferred is tetrahydrofuran. A catalytically effective amount of a chiral oxazaborolidine compound of formula I is added to the reaction mixture at from about –78° C. to about room temperature, preferably at room temperature; however, the preferred temperature will vary depending upon the particular borane reducing agent being used. The preferred amount of said catalyst is about 5–10 mole % with respect to said ketone. The reaction mixture is then treated slowly with about 2.1 hydride equivalents of a borane reducing agent such as borane dimethylsulfide complex, borane tetrahydrofuran complex, catecholborane or the like. When the prochiral ketone contains an $R^4$ or $R^5$ group which bears a borane-coordinating functionality, additional hydride equivalents of reducing agent are necessary. Generally preferred for its ease of use is borane dimethylsulfide complex. Generally the reducing agent is added at a rate which modulates the rate of the catalytic reduction. The reaction is sometimes complete as soon as all of the reducing agent has been added, as can be determined by monitoring the course of the reaction via thin layer chromatography according to the standard practice of organic chemistry. However, occasionally it will be desirable to allow the reaction mixture to stir for longer periods of time such as overnight, or to heat the reaction mixture to temperatures of up to 40° C. to 65° C. in order to ensure completion of the reaction. Additionally, with some substrates and reducing agents, it may be necessary to stir the reaction mixture at –78° C. for a lengthy period of time such as 16 hours. Ordinarily the reaction mixture is stirred at about room temperature for about fifteen minutes. The temperature of reaction mixture is then adjusted to 0° C. and quenched with a proton source. Said proton source, usually a lower alkanol such as methanol, is added slowly to prevent an exothermic reaction. The product is isolated by removing the solvent in vacuo followed by partitioning between an organic solvent and an aqueous acid followed by separation of layers and purification according to the standard techniques of organic chemistry.

The prochiral ketone may be any compound of the formula $R^4R^5CO$ wherein $R^4$ and $R^5$ are different and wherein $R^4$ and $R^5$ are inert to reduction by borane. Additionally, if enough reducing agent is utilized to account for the presence of borane coordinating substituents on $R^4$ or $R^5$, then $R^4$ or $R^5$ may be thus substituted. Thus, $R^4$ and $R^5$ may independently be any organic radicals, e.g. alkyl, aryl, alkenyl and may be taken together to form a ring system so that $R^4R^5CO$ is cyclic, e.g. tetralone. Additionally, $R^4$ and $R^5$ may be independently substituted with any substituents such as alkyl, alkenyl, aryl, alkoxy, halo, etc. It will be understood by one of ordinary skill in the art that when $R^4$ or $R^5$ contains an alkenyl substituent it will be necessary to choose a borane reducing agent which is not capable of hydroborating the olefin. Further, said $R^4$ and $R^5$ groups may be substituted with boron-coordinating substituents provided that enough reducing agent is utilized to account for such substitution. Examples of borane-coordinating substituents such as certain heteroaryl groups which may be present include thiazolyl, oxazolyl, pyridyl and the like. One of ordinary skill in the art would recognize that additional equivalents of borane reducing agent will be necessary when borane-coordinating substituents are present on said $R^4$ or $R^5$ groups.

The compound of formula II of the present invention is a reaction intermediate which exists during the course of the reaction. The compound is formed upon the addition of the borane reducing agent to the reaction mixture containing the oxazaborolidine catalyst and the substrate and is a result of the reaction of said catalyst with said borane reducing agent.

Thus, the oxazaborolidine compounds are useful as enantioselective catalysts for the reduction of prochiral ketones to afford substantially enantiomerically pure alcohols. The process of preparing said alcohols has great utility since the optically pure form of a compound often has far different reactivity or usefulness in biological systems. The optically pure alcohols thus prepared may find utility as intermediates in the synthesis of a pharmaceutical, agricultural or other useful product. The optically pure alcohols thus prepared may themselves be useful as pharmaceuticals, agricultural products or the like.

The following terms and phrases, when used herein, are defined as follows:

1. "Alkyl" means a branched or unbranched saturated hydrocarbon group containing the specified number of carbon atoms, e.g., $C_1$–$C_8$. Examples include, but are not limited to methyl, ethyl, n-butyl and the like.
2. "Alkenyl" means a branched or unbranched unsaturated hydrocarbon group containing one or more double bond(s) and the specified number of carbon atoms, e.g., $C_2$–$C_4$. Examples include, but are not limited to vinyl, ethylidene, allyl and the like.
3. "Alkoxy" means a branched or unbranched saturated hydrocarbon containing a single oxygen atom by which said hydrocarbon is attached to a central backbone. Examples include, but are not limited to methoxy, ethoxy and the like.
4. "Aryl" means an aromatic hydrocarbon containing the specified number of carbon atoms said aryl group being optionally substituted with up to three substituents each independently selected from ($C_1$–$C_8$)alkyl, ($C_1$–$C_8$)alkoxy and halo. Examples include, but are not limited to, phenyl, naphthyl and the like.
5. "Heteroaryl" means a 5- or 6-membered aromatic heterocyclic group containing up to three heteroatoms, each selected from N, O and S and which may be optionally benzo-fused said heteroaryl group being optionally substituted with up to three ($C_1$–$C_8$)alkyl, ($C_1$–$C_8$)alkoxy and halo. Examples include, but are not limited to thiazolyl, oxazolyl, pyridyl and the like.
6. A "prochiral ketone", denoted by $R^4R^5CO$, is a ketone in which $R^4$ and $R^5$ are non-identical, so that the secondary alcohol reduction product $R^4R^5CHOH$ has a chiral center at the alcohol carbon.
7. Reaction inert solvent means a solvent which does not interact with the reactants, intermediates or products in such a way that adversely affects the yield of the desired products.
8. "Syn" means that the substituents substituted on adjacent ring carbon atoms are located on the same side of a plane which encompasses the bond between said carbon atoms and the bonds by which each of said carbon atoms are attached to the ring.
9. "Enantiomeric excess", or e.e., is the excess of one of two enantiomers over the other, usually expressed as a percentage, i.e., a 90% e.e. reflects the presence of 95% of one enantiomer and 5% of the other in the material in question.
10. A "borane-coordinating substituent" is a functional group which has the ability to donate an electron pair to boron forming a coordinate bond with said boron. Typical examples include, but are not limited to, amines and various nitrogen-containing heterocycles.
11. "Hydride equivalents" means the number of hydride, or $H^\ominus$, ions which are generated from one mole of a given reagent, e.g., one mole of borane-tetrahydrofuran complex generates three moles of hydride ion and is thus considered to contain three hydride equivalents.
12. "Catalytically effective" means that sub-stoichiometric amount of a material which is sufficient to facilitate the conversion of a reactant to the desired product(s).
13. "Ambient temperature" means the temperature of the immediate external environment surrounding the reaction flask. This temperature is usually room temperature.

The present invention is illustrated by the following examples. However, it should be understood that the invention is not limited to the specific details of these examples. All reactions are conducted under an inert atmosphere, such as nitrogen or argon, unless otherwise specified. All solvents are anhydrous, i.e., contain such a small amount of water that said water does not interact with the reagents, intermediates or products in such a way that adversely affects the yield of the desired products. Where used herein, "THF" means tetrahydrofuran.

EXAMPLE 1

(4R, 5S)-(+)-4,5-Diphenyl-2-methyl oxazaborolidine (1R, 2S)-(−)-2-Amino-1,2-diphenylethanol (4.9 g, 0.0229 moles) was suspended in toluene (150 mL) and heated to 80° C. to afford a colorless solution. The reaction mixture was treated all at once with trimethylboroxine (2.13 mL, 0.015 moles) and the heating bath was removed. The reaction mixture was stirred for 18 hours at ambient temperature. After 18 hours, the toluene and excess trimethylboroxine and water were distilled off until only 65 ml remained. The reaction was chased with toluene (3×60 ml) each time distilling until 65 ml remained. After the third time the remaining toluene was distilled off at atmospheric pressure and then under high vacuum to yield an off-white solid. mp 69°–70° C., $[\alpha]_D$=+65 (C=2, toluene).

EXAMPLE 2

(4R, 5S)-(+)-2,4,5-Triphenyl oxazaborolidine

To a solution of (1R, 2S)-(−)-2-amino-1,2-diphenylethanol (4.126 g, 0.019 moles) in benzene (100 mL) was added triphenyl boroxine (2.055 g, 0.0064 moles). The reaction mixture was heated under reflux for 16 hours with a Dean-Stark trap to remove water. The benzene was removed by atmospheric distillation to remove most of the solvent. The remainder of the solvent was removed under high vacuum to afford 5.68 g (98%) of the product as a thick pale yellow oil which solidified to a wax upon standing at ambient temperature. $[\alpha]_D$=−98.0 (C=1.20, toluene).

EXAMPLE 3

(4S,5R)-(−)-4,5-Diphenyl-2-methyl oxazaborolidine

Using substantially the same procedure as recited in Example 1, but substituting (1S,2R)-(+)-2-amino-1,2-diphenylethanol for (1R,2S)-(−)-2-amino-1,2-diphenyl ethanol, the title compound of Example 3 was prepared.

EXAMPLE 4

(R)-(+)-1,2,3,4-Tetrahydro-1-naphthol

Borane dimethylsulfide complex (2M in THF, 7.0 mL, 0.014 moles) was added over 45 minutes at ambient temperature to a solution of α-tetralone (2.92 g, 0.02 moles) and the title compound of Example 1 (247 mg, 0.001 moles) in THF (80 mL). The reaction mixture was stirred for 15 minutes (at which time thin layer chromatography indicated complete consumption of α-tetralone) and then cooled to 0°

C. and quenched with methanol 27 mL). The quenched solution was allowed to warm to ambient temperature, with stirring, for 16 hours. The solvents were removed in vacuo and the residue was redissolved with methylene chloride (50 mL) and pH4 phosphate buffer (50 mL). The phases were separated and the organic phase was washed with water (50 mL), treated with MgSO$_4$ and filtered. The solvent was removed in vacuo to afford 2.93 (99%) of -(R)-(+)-1,2,3,4-tetrahydro-1-naphthol as a white solid. HPLC with a chiral support demonstrated that the product had a 94% e.e.

EXAMPLES 5–11

Using substantially the same procedure as recited in Example 4 but substituting the appropriate prochiral ketone for α-tetralone and utilizing an appropriate amount of reducing agent, the following compounds were prepared.

| Product | Equivalents of BH$_3$/DMS | % ee |
|---|---|---|
| 5. R-(1)-1-indanol | 0.7 | 90 |
| 6. (R)-(sec)-phenethyl-alcohol | 0.7 | 92 |
| 7. (R)-3,3-dimethyl-2-butanol | 0.7 | 88 |
| 8. (R)-4-chromanol | 0.7 | 96 |
| 9. (R)-3-(1-hydroxyethyl)pyridine | 1.7 | 80 |
| 10. (R)-1-cyclohexylethanol | 0.7 | 62 |
| 11. (R)-1-phenyl-1-propyl-alcohol | 0.7 | 82 |

EXAMPLE 12

(R)-(+)-1,2,3,4-Tetrahydro-1-naphthol

Using substantially the same procedure as recited in Example 4 but substituting the title compound of Example 2 for the title compound of Example 1, the title compound of Example 12 was prepared in 88% e.e.

EXAMPLE 13

(S)-5-[4-(3-(5-methyl-2-phenyl-4-oxazolyl)-1-hydroxypropyl)benzyl]thiazolidine- 2,4-dione Using substantially the same procedure as recited in Example 4 but substituting the title compound of Example 3 for the title compound of Example 1 and substituting the title compound of Preparation 1 for α-tetralone, the title compound of Example 13 was prepared in 78% e.e.

EXAMPLE 14

(R)-4-(2-Bromo)-1-hydroxyethyl-2-trifluoromethylthiazole

Using substantially the same procedure as recited in Example 4 but substituting the title compound of Example 3 for the title compound of Example 1 and substituting the title compound of Preparation 2 for α-tetralone, the title compound of Example 14 was prepared in 78% e.e.

Preparation 1

5-[4-(3-(5-Methyl-2-phenyl-4-oxazolyl)propionyl)-benzyl]thiazolidine-2,4-dione

The title compound of this preparation was prepared as described in Clark, et al., U.S. Pat. No. 5,036,079.

Preparation 2

4-Bromoacetyl-2-trifluoromethylthiazole

The title compound of this preparation was prepared as described in Reiffen, U.S. Pat. No. 4,886,814.

I claim:
1. A chiral 1,3,2-oxazaborolidine of the formula

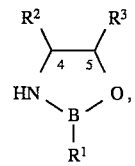

wherein:
R$^1$ is hydrogen, (C$_1$–C$_8$)alkyl, benzyl, phenyl or phenyl substituted with up to three (C$_1$–C$_8$)alkyl, (C$_1$–C$_8$)alkoxy or halo; and R$^2$ and R$^3$ are syn and are each identically phenyl or phenyl substituted with up to three (C$_1$–C$_8$)alkyl, (C$_1$–C$_8$)alkoxy or halo.

2. A chiral oxazaborolidine according to claim 1 wherein the C$_4$ carbon atom has the R configuration and the C$_5$ carbon atom has the S configuration.

3. A chiral oxazaborolidine according to claim 2 wherein R$^2$ and R$^3$ are each phenyl.

4. The chiral oxazaborolidine according to claim 3 wherein R$^1$ is methyl.

5. A chiral oxazaborolidine according to claim 1 wherein the C$_4$ carbon atom has the S configuration and the C$_5$ carbon atom has the R configuration.

6. A chiral oxazaborolidine according to claim 5 wherein R$^2$ and R$^3$ are each phenyl.

7. The chiral oxazaborolidine according to claim 6 wherein R$^1$ is methyl.

8. A compound of the formula

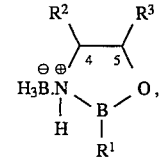

wherein:
R$^1$ is hydrogen, (C$_1$–C$_8$)alkyl, benzyl, phenyl or phenyl substituted with (C$_1$–C$_8$)alkyl, (C$_1$–C$_8$)alkoxy or halo; and R$^2$ and R$^3$ are syn and are each identically phenyl or phenyl substituted with up to three (C$_1$–C$_8$)alkyl, (C$_1$–C$_8$)alkoxy or halo.

9. The compound of formula 8, wherein R$^1$ is methyl, R$^2$ and R$^3$ are each phenyl, the C$_4$ carbon atom has the R configuration and the C$_5$ carbon atom has the S configuration.

10. The compound of formula 8, wherein R$^1$ is methyl, R$^2$ and R$^3$ are each phenyl, the C$_4$ carbon atom has the S configuration and the $C_5$ carbon atom has the R configuration.

11. A method for steroselectively reducing a prochiral ketone to a substantially enantiomerically pure alcohol comprising reacting said prochiral ketone with a borane reducing agent in the presence of a chiral oxazaborolidine according to claim 1.

* * * * *